United States Patent [19]
Law et al.

[11] Patent Number: 5,286,626
[45] Date of Patent: Feb. 15, 1994

[54] PROCESS AND APPARATUS FOR DIRECT DETERMINATION OF LOW DENSITY LIPOPROTEIN

[75] Inventors: Wai T. Law, Sewell; Gerhard Ertingshausen, Princeton, both of N.J.

[73] Assignee: ActiMed Laboratories, Inc., Mt. Laurel, N.J.

[21] Appl. No.: 806,183

[22] Filed: Dec. 13, 1991

[51] Int. Cl.$^5$ .......................... C12Q 1/44; C12M 3/04; G01N 31/00
[52] U.S. Cl. ..................................... 435/19; 435/285; 436/13
[58] Field of Search ...................... 435/19, 285; 436/13

[56] References Cited

U.S. PATENT DOCUMENTS

| | | | |
|---|---|---|---|
| 4,126,416 | 11/1978 | Sears | 23/230 B |
| 4,210,557 | 7/1980 | Handschuh | 436/13 |
| 4,366,244 | 12/1982 | Pascal | 435/25 |
| 4,474,887 | 10/1984 | Maier et al. | 436/71 |
| 4,486,531 | 12/1984 | Ziegenhorn et al. | 435/19 |
| 4,647,280 | 3/1987 | Maaskant et al. | 604/5 |
| 4,746,605 | 5/1988 | Kerscher et al. | 435/19 |

Primary Examiner—John W. Rollins
Attorney, Agent, or Firm—Iver P. Cooper

[57] ABSTRACT

Low density lipoprotein are directly determined in body fluids by selectively precipitating very low density lipoprotein, forming clusters with low density lipoproteins, selectively consuming the high density lipoproteins, and resolubilizing the low density lipoproteins for direct determination thereof. The clusters are formed by treating the fluid sample with a mixture of a polyanionic compound, a divalent metal, and a nucleating agent.

12 Claims, 1 Drawing Sheet

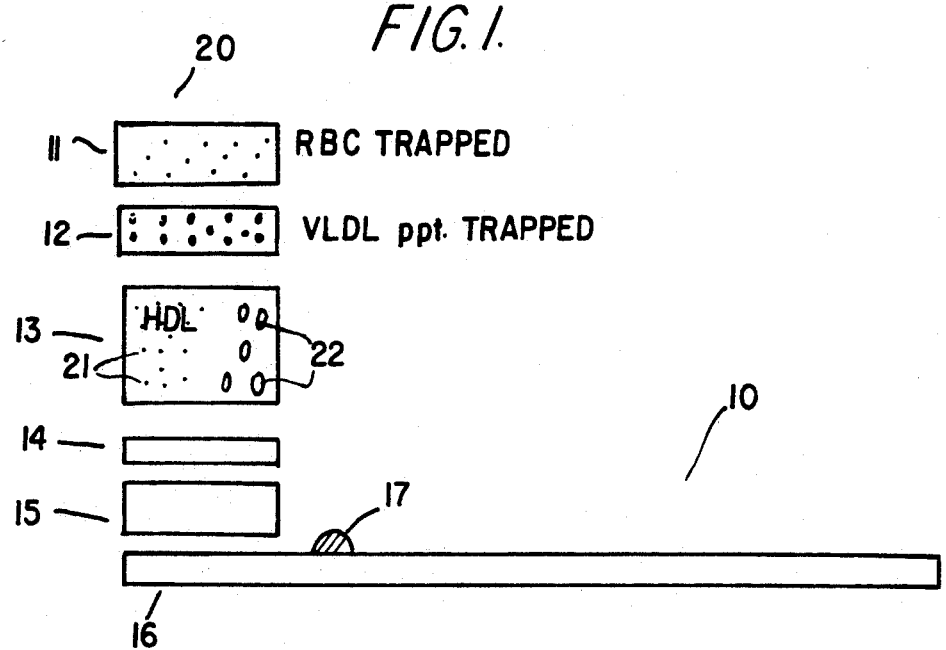
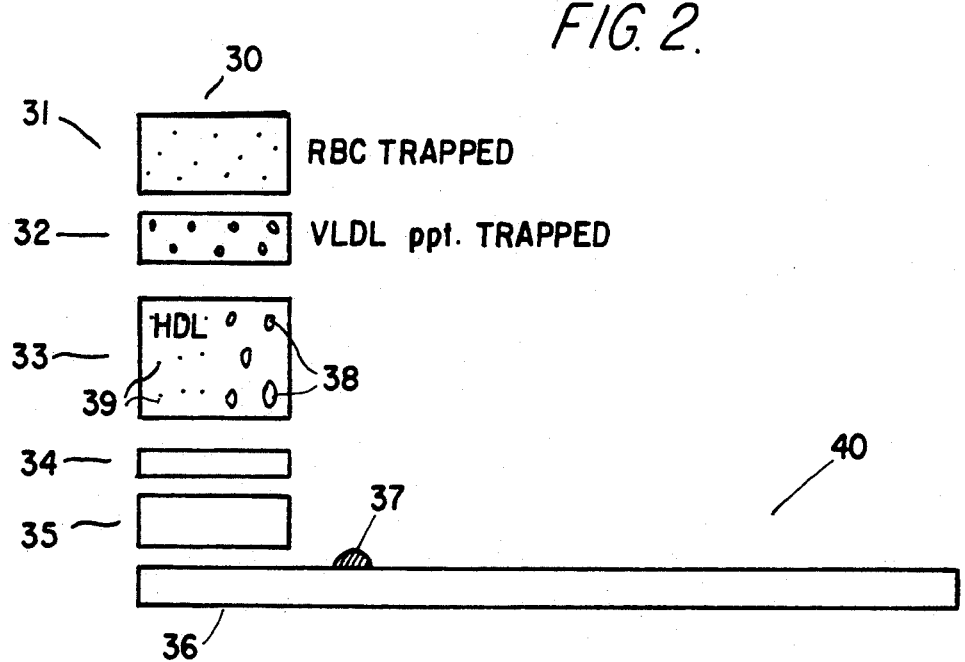

PROCESS AND APPARATUS FOR DIRECT DETERMINATION OF LOW DENSITY LIPOPROTEIN

FIELD OF THE INVENTION

The present invention relates to a process for the direct determination of low density lipoprotein in body fluids. More specifically, the present invention relates to a process and apparatus for determination of low density lipoprotein by selectively precipitating low density lipoprotein from a sample, providing enzymes which selectively consume the high density lipoprotein, and then resolubilizing the low density fraction and determining this fraction enzymatically.

BACKGROUND OF THE INVENTION

Lipoproteins are complex particles consisting of protein and lipid which are found in the circulatory system. One of their functions is to carry water-insoluble substances such as cholesterol and cholesterol esters for eventual cellular utilization. While all cells require cholesterol for growth, excess accumulation of cholesterol by cells is known to lead to certain diseases, including atherosclerosis.

It is known that the amount of total serum cholesterol can be correlated with the incidence of atherosclerosis. However, there are a variety of classes of lipoproteins in serum which can be classified by their density. These classes include very low density lipoproteins (VLDL), low density lipoproteins (LDL), and high density lipoproteins (HDL). All of these lipoprotein classes contain varying amounts of cholesterol, and a total serum cholesterol determination is a complex average of the amount that each lipoprotein class contributes to the total lipoprotein population of the serum.

It has long been suspected that specific lipoprotein classes were more closely associated than other lipoprotein classes with the progression of heart disease, including atherosclerosis. In fact, more recent studies have implicated LDL as the class of lipoproteins responsible for the accumulation of cholesterol in cells, whereas HDL has been shown to be important in the removal of excess cholesterol from cells. Additionally, the correlation of atherosclerosis and the levels of LDL cholesterol is much higher than a similar correlation between atherosclerosis and total serum cholesterol levels. Conversely, there appears to be a negative correlation of atherosclerosis and HDL cholesterol levels.

Despite the desirability of isolating LDL cholesterol levels in blood plasma from other soluble cholesterols, a technique suitable for use in clinical laboratories has not heretofore existed. One method which has been suggested relies upon the interaction of heparin in the presence of calcium to precipitate both LDL and VLDL, cf. Bursterin et. al., *Adv. Lipid Res.* 11: 67 (1973). To separate the LDL and VLDL fractions, ultracentrifugation techniques, which are time consuming and expensive, must be used.

Another method for determining LDL is calculation by the Friedewald Formula, as disclosed in Friedewald et al., *Clin. Chem.* 18: 499-502 (1972). In this method, LDL is estimated by the total cholesterol, HDL, and triglyceride contents of the sample. This method requires multiple assays, and is not accurate for samples containing high levels of triglycerides.

Ultracentrifugation, to separate the lipoproteins solely on the basis of their density, requires special equipment and long processing time. Electrophoretic separation also requires special equipment and long processing times.

A variety of precipitation methods have been used, which depend upon the use of polyanions and divalent cations. Okabe Xth Int. Cong. of Clin. Chem., Mexico (1978); Genzyme Diagnostics, Cambridge, Mass. LDL cholesterol precipitation reagent package insert. Other precipitation methods use polymers, as shown in U.S. Pat. No. 4,474,898 and U.S. Pat. No. 4,647,280; or lectin, as disclosed in U.S. Pat. No. 4,126,416. Kerscher et al., in U.S. Pat. No. 4,746,605, teach that VLDL and HDL can be precipitated by HDL antibodies with polyanions and divalent cations. However, the amount of antibodies required with this method is too expensive for routine use.

When LDL is precipitated with polyanions such as dextran sulfate and divalent cations such as magnesium, the precipitate redissolves if one tries to selectively convert the cholesterol in the supernatant by an enzymatic assay which requires the presence of surfactants. Moreover, LDL in the presence of the enzyme cholesterol esterase and cholesterol oxidase, is hydrolyzed thereby.

Consequently, there is a need for a simple procedure or device for the determination of LDL lipoprotein accurately.

SUMMARY OF THE INVENTION

It is an object of the present invention to overcome the aforementioned deficiencies in the prior art.

It is another object of the present invention to provide a simple method for the determination of LDL.

It is a further object of the present invention to provide an apparatus for determination of LDL.

According to the present invention, LDL can be precipitated with a mixture of large polyanions and divalent cations in the presence of a small amount of nucleating particles. These particles may range in size from about 0.1 to about 200 microns, and may be either mixed with the polyanionic compound or the polyanionic compound may be immobilized thereon.

An LDL precipitate is formed in the presence of the nucleating particles and polyanionic molecule, which precipitate is not hydrolyzed at a noticeable rate by the enzyme cholesterol esterase in the presence of surfactants. The nucleating agents aid in the formation of large clusters of LDL precipitates, and also help to stabilize the clusters against the effect of surfactants and cholesterol esterase.

Both of the above phenomena were surprising because LDL precipitate normally dissolves quickly in the presence of surfactants such as sodium cholate, and cholesterol esterase usually hydrolyzes any cholesterol esters in lipoproteins rapidly in the presence of suitable surfactants. However, the presence of sufficient small particles to provide nucleating agents for clusters of LDL stabilized the clusters against the effect both of surfactants and of cholesterol esterase.

BRIEF DESCRIPTION OF THE DRAWINGS

FIG. 1 is a side view of a direct LDL measurement device according to the present invention.

FIG. 2 is a side view of another direct LDL measurement device according to the present invention.

DETAILED DESCRIPTION OF THE INVENTION

Referring to FIG. 1, the device according to the present invention is shown at 10. A fluid sample is introduced to the device 10 at 20, and red blood cells are trapped in layer 11. Plasma then enters layer 12, where all of the VLDL is trapped as a precipitate in layer 12. Plasma containing all of the HDL and LDL then enters zone 13. A particle enhanced LDL precipitation reagent 21 in zone 13 causes the LDL to precipitate in large clusters 22 in less than 60 seconds. The enzymes cholesterol esterase (CE) and cholesterol oxidase (CO), together with the surfactants deposited in zone 13, react with the HDL to produce hydrogen peroxide. Surprisingly, the particle enhanced LDL precipitate 22 does not dissolve and does not react with the cholesterol enzymes, so that only the HDL reacts with the cholesterol enzymes, and the hydrogen peroxide generated thereby is consumed by endogenous catalase in less than ten minutes.

Zone 14 is a thin sucrose coating and is designed to dissolve in less than ten minutes. Zone 15 contains dried hydroxylamine (HA), which is a catalase inhibitor, and protease, which reacts with the protein moiety of LDL. When zone 14 is dissolved, both the hydroxylamine and the protease are mixed with the contents of zone 13, where the catalase is inhibited by hydroxylamine and the LDL clusters are then dissolved by the action of protease. The re-dissolved LDL then reacts with cholesterol oxidase and cholesterol esterase, generating hydrogen peroxide which flows through a timing barrier 17 into the measurement zone 16 on the device. The length of the color bar developed in the measurement zone is proportional to the concentration of the LDL in the whole blood sample.

More specifically, during the first ten minutes, the reactions in zone 13 are as follows:

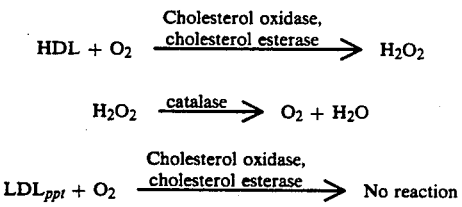

During the next five minutes, the reactions in layer 13 are as follows:

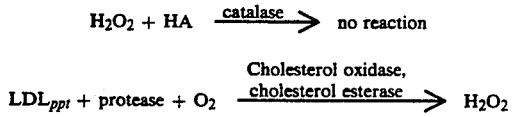

The device of the present invention can be used with a different enzyme system, as shown in FIG. 2. In FIG. 2, whole blood is introduced into the device 40 at 30, the top of layer 31. Red blood cells are trapped in zone 31, and plasma enters zone 32. A VLDL precipitation reagent in zone 32 traps all VLDL, and plasma containing HDL and LDL enters zone 33. A particle enhanced LDL precipitation reagent 38 in zone 33 causes LDL to precipitate in large clusters 38 in less than 60 seconds. In addition, zone 33 is buffered to about pH 9, and contains cholesterol esterase, cholesterol oxidase, cholesterol dehydrogenase (CDH), protease, NAD, surfactants and cation exchange resins. HDL in the plasma reacts with cholesterol esterase, cholesterol dehydrogenase and NAPD to produce NAPDH, while the LDL precipitate remains unaffected. The pH in zone 33 drops with time because of the cation exchange resins which become bedded inside this zone. Additionally, as the pH falls from 9.0 to 7.0, the cholesterol dehydrogenase becomes inactivated, while the cholesterol oxidase and protease become activated. The LDL precipitate is then dissolved by the protease, and cholesterol esterase and cholesterol oxidase react with LDL to generate hydrogen peroxide. The hydrogen peroxide so generated flows through the timing barrier 37 into measurement zone 36. The length of the color bar developed in the measurement zone is proportional to the concentration of the LDL in the whole blood sample.

Of course, it will be appreciated that the devices specifically disclosed herein for use in assaying for low density lipoprotein are not the only devices in which the system for assaying for low density lipoprotein can be used. The system can be used with any suitable device which provides a means for trapping the VLDL precipitate and for forming clusters of LDL which can be separated from HDL for analysis.

Alternatively, instead of sequentially precipitating VLDL and LDL, a specific LDL precipitating reagent with added nucleating particles can be used. In this case, the HDL and VLDL in the supernatant react with the cholesterol enzymes first, and LDL reacts after the HA and protease are released.

The polyanions that can be used for forming the LDL clusters can be any suitable polyanions for use in clinical assays and which do not interfere with subsequent enzymatic or other assays for LDL. Among the polyanions that can be used are dextran sulfate, heparin, phosphotungstic acid, and polyvinyl sulfate. The dextran sulfate can be high molecular (i.e., molecular weight of from $5 \times 10^4$ to $2 \times 10^6$) or short-chained (molecular weight of from 5000 to 50,000). The preferred concentration ranges of the polyanions in the reaction mixture are from about 0.1 to about 8 g/liter in the case of high molecular weight dextran sulfate, from about 1 to about 15 g/liter in the case of short-chained dextran sulfate and heparin, from about 0.2 to about 5 g/liter in the case of polyvinyl sulfate, and from about 0.3 to about 6 g/liter in the case of phosphotungstic acid.

The polyvinyl sulfate is a polymer derived from polyvinyl alcohol, of which polymer at least 20% of the vinyl alcohol groups are sulfated. The molecular weight of the polyvinyl alcohol is not critical as long as it can be crosslinked. This is generally the case at a molecular weight of about 5000 or higher. Very favorable results can be obtained at molecular weights in the range of 10,000 to 150,000 or more.

For best results, at least 50% of the vinyl groups are sulfated. Optimum results are obtained wherein at least about 65% of the vinyl alcohol groups are sulfated. Sulfation of the polyvinyl alcohol is preferably carried out using a reaction product of sulfur trioxide or chlorsulfonic acid and a Lewis base. Particularly suitable is the addition product of pyridine to sulfur trioxide. The sulfation reaction is preferably carried out in dimethyl formamide or formamide at a temperature of between 60° and 110° C. The polyvinyl alcohol may be crosslinked before or after sulfation and the crosslinking may be effected either chemically or physically.

The divalent cations that can be used in the system of the present invention include calcium, magnesium and manganese. These cations can be added in the form of a salt such as a chloride salt. The concentration of the divalent metal ions to be added is preferably from about 10 to about 250 mMole/liter in the reaction mixture. Furthermore, the reaction mixture preferably contains sodium chloride in a concentration of from 0.1 to 1 mole/liter. A conventional buffer can be used to buffer in a pH range of from about 6.5 to about 8.5, such as MES (morpholino ethane sulfonic acid), triethanolamine, MOPS (morpholino propane sulfonic acid) or Tris buffer.

Once the LDL fraction has been separated from the other components in the sample, conventional methods of analysis can be used for the LDL determination. The LDL determination can, for example, take place by saponification with alcoholic potassium hydroxide solution and chemical determination according to Liebermann-Burchard. However, it is preferred to use an enzymatic determination using cholesterol oxidase and a cholesterol ester-splitting enzyme or enzyme system, such as cholesterol esterase. In the case of the use of cholesterol esterase, the determinations can be based upon the amount of oxygen consumed, the amount of cholestenon formed, or the amount of hydrogen peroxide formed using conventional methods for this purpose. Since the determination of bound cholesterol is well known, there is no need to describe it in detail.

The particles that can be used as nucleating agents for forming the LDL clusters can be any particles that do not interfere with the subsequent assay for LDL. For example, chromium dioxide, stainless steel, silicon dioxide, glass, methyl methacrylate particles, and the like can all be used. The particle size is generally between about 0.5 and 100 microns.

The nucleating agents can be added in with a mixture of the polyanionic compound and the divalent metal. Alternatively, the nucleating agents can be coated with the polyanionic compound or various compounds and added along with the divalent metal to the fluid sample.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

What is claimed is:

1. A process for direct determination of low density lipoprotein in a fluid sample comprising:
   selectively precipitating very low density lipoprotein from the fluid sample;
   adding a polyanionic compound, a salt of a divalent metal and a nucleating agent to the fluid sample to form clusters of low density lipoprotein;
   adding an enzyme selected from the group consisting of cholesterol oxidase, cholesterol esterase, and mixtures thereof to consume high density lipoprotein selectively from the fluid sample;
   contacting said sample with a protease for resolubilizing the low density lipoprotein;
   and contacting said fluid sample with reagents for determining the amount of low density lipoprotein in the sample.

2. The process according to claim 1 wherein said polyanionic component is selected from the group consisting of dextran sulfate, heparin, phosphotungstic acid, and polyvinyl sulfate.

3. The process according to claim 1 wherein said divalent cations are selected from the group consisting of calcium, manganese and magnesium.

4. The process according to claim 1 wherein said nucleating agents are selected from the group consisting of stainless steel particles, silicon dioxide particles, and polymethyl methacrylate particles.

5. The process according to claim 4 wherein said nucleating agents have a particle size ranging from about 0.1 to 200 microns.

6. The process according to claim 1 wherein said low density lipoprotein is determined enzymatically.

7. A process for direct determination in a measurement device of low density lipoprotein in a fluid sample comprising:
   providing a measurement device having first and second zones;
   introducing said sample into a first zone of said device wherein said sample contacts a mixture of a polyanionic compound, a salt of a divalent metal, and a nucleating agent to form clusters of low density lipoprotein;
   introducing said sample into a second zone of said device wherein said sample contacts an enzyme selected from the group consisting of cholesterol oxidase, cholesterol esterase, and mixtures thereof and to consume high density lipoprotein and very low density lipoprotein selectively from the fluid sample; contacting said sample with a protease to resolubilize low density lipoprotein; and determining the amount of low density lipoprotein in the sample.

8. The process according to claim 7 wherein said polyanionic component is selected from the group consisting of dextran sulfate, heparin, phosphotungstic acid, and polyvinyl sulfate.

9. The process according to claim 7 wherein said divalent cations are selected from the group consisting of calcium, manganese and magnesium.

10. The process according to claim 7 wherein said nucleating agents are selected from the group consisting of stainless steel particles, silicon dioxide particles, and polymethyl methacrylate particles.

11. The process according to claim 7 wherein said low density lipoprotein is determined enzymatically.

12. The process according to claim 7 wherein said nucleating agents have a particle size ranging from about 0.1 to 200 microns.

* * * * *